(12) United States Patent
Huang

(10) Patent No.: US 12,023,673 B2
(45) Date of Patent: Jul. 2, 2024

(54) BRANCHED NANOCHANNEL DEVICES FOR DETECTION AND SORTING OF NUCLEIC ACIDS

(71) Applicant: The Board of Trustees of the University of Alabama, Tuscaloosa, AL (US)

(72) Inventor: Qiang Huang, Tuscaloosa, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 677 days.

(21) Appl. No.: 17/199,656

(22) Filed: Mar. 12, 2021

(65) Prior Publication Data

US 2021/0197198 A1 Jul. 1, 2021

Related U.S. Application Data

(62) Division of application No. 15/875,248, filed on Jan. 19, 2018, now Pat. No. 10,974,244.
(Continued)

(51) Int. Cl.
| | |
|---|---|
| *C12Q 1/6825* | (2018.01) |
| *B01L 3/00* | (2006.01) |
| *C25D 1/00* | (2006.01) |
| *C25D 1/04* | (2006.01) |
| *G01N 27/447* | (2006.01) |
| *G01N 33/487* | (2006.01) |
| *C23F 1/16* | (2006.01) |
| *C25D 3/56* | (2006.01) |

(52) U.S. Cl.
CPC ... *B01L 3/502761* (2013.01); *B01L 3/502707* (2013.01); *C12Q 1/6825* (2013.01); *C25D 1/006* (2013.01); *C25D 1/04* (2013.01); *G01N 27/44704* (2013.01); *G01N 27/44791* (2013.01); *G01N 33/48721* (2013.01); *B01L 2200/0652* (2013.01); *B01L 2200/0663* (2013.01); *B01L 2200/12* (2013.01); *B01L 2300/0645* (2013.01); *B01L 2300/0816* (2013.01); *B01L 2300/0864* (2013.01); *B01L 2300/087* (2013.01); *B01L 2300/0896* (2013.01); *B01L 2400/0421* (2013.01); *C23F 1/16* (2013.01); *C25D 3/56* (2013.01); *C25D 3/562* (2013.01)

(58) Field of Classification Search
None
See application file for complete search history.

(56) References Cited

U.S. PATENT DOCUMENTS

| | | | |
|---|---|---|---|
| 9,017,937 B1 * | 4/2015 | Turner | C12Q 1/6869 435/6.1 |
| 2006/0073489 A1 | 4/2006 | Li et al. | |

(Continued)

OTHER PUBLICATIONS

Beaucage and Carruthers, "Deoxynucleoside phosphoramidites—A new class of key intermediates for deoxypolynucleotide synthesis", Tetrahedron Lett., 22:1859-1862 (1981).
(Continued)

*Primary Examiner* — Robert T. Crow
(74) *Attorney, Agent, or Firm* — Meunier Carlin & Curfman LLC

(57) ABSTRACT

The present disclosure relates to devices and methods for the detection and/or sorting of nucleic acids. Further disclosed are methods for device fabrication.

20 Claims, 11 Drawing Sheets

Related U.S. Application Data

(60) Provisional application No. 62/448,115, filed on Jan. 19, 2017.

(56) References Cited

U.S. PATENT DOCUMENTS

| | | |
|---|---|---|
| 2009/0305273 A1 | 12/2009 | Cao et al. |
| 2011/0053284 A1 | 3/2011 | Meller et al. |
| 2011/0108423 A1* | 5/2011 | Van Der Zaag ............................ G01N 33/48721 977/924 |
| 2013/0256118 A1 | 10/2013 | Meller et al. |

OTHER PUBLICATIONS

Matteucci, et al., "Synthesis of deoxyoligonucleotides on a polymer support", J. Am. Chem. Soc., 103:3185-3191 (1981).

* cited by examiner

Top down diagram

Cross sectional view at A - A'

BRANCHED NANOCHANNEL DEVICES FOR DETECTION AND SORTING OF NUCLEIC ACIDS

CROSS REFERENCE TO RELATED APPLICATIONS

This application is a divisional of U.S. application Ser. No. 15/875,248 filed Jan. 19, 2018, which claims the benefit of U.S. Provisional Patent Application Ser. No. 62/448,115 filed Jan. 19, 2017, the disclosures of which are expressly incorporated herein by reference.

FIELD

The present disclosure relates to devices and methods for the detection and/or sorting of nucleic acids. Further disclosed are methods for device fabrication.

BACKGROUND

Gene detection is of great interest for human health, including genetic disease diagnosis, as well as various applications in fundamental research in genetic engineering. The methods that are available typically require amplification of nucleic acids and require a large amount of DNA, resulting in averaged signals. Furthermore, these methods typically do not determine the location of the target genes on DNA molecules. In addition, confirmation of correct genome editing typically relies on the expression of genes in microorganisms, which can take many weeks or even months. Techniques for the quick and accurate detection of the presence and location of genes on DNA at the single molecule level are desired.

The compounds, compositions, and methods disclosed herein address these and other needs.

SUMMARY

Disclosed herein are branched nanochannel devices and methods for the detection and/or sorting of nucleic acids. Further disclosed are methods for the fabrication of branched nanochannel devices.

In one aspect, disclosed herein is a device comprising:
a branched nanochannel;
three or more fluid chambers connected by the branched nanochannel; and
three or more nanopores in the branched nanochannel;
wherein two or more nanopores are adjacent to each other on different branches of the branched nanochannel.

In one embodiment, the device further comprises an electrode within each of the three or more fluid chambers.

In one embodiment, the nanopores are dimensioned to allow a linearized nucleic acid to pass through the nanopores. In one embodiment, the nanopores have a diameter from 2 nm to 100 nm. In one embodiment, the nanopores have a diameter from 10 nm to 20 nm.

In one embodiment, the adjacent nanopores are from 0.5 µm to 10 µm apart. In one embodiment, the adjacent nanopores are from 1 µm to 3 µm apart.

In one embodiment, the nanochannel has a diameter from 50 nm to 1000 nm. In one embodiment, the nanochannel has a diameter from 200 nm to 400 nm. In one embodiment, the nanochannel has a length from 5 µm to 100 µm. In one embodiment, the nanochannel has a length from 10 µm to 30 µm.

In another aspect, disclosed herein is a method for detecting a nucleic acid, comprising: introducing a nucleic acid into a fluid chamber of a device, wherein the device comprises:
a branched nanochannel;
three or more fluid chambers connected by the branched nanochannel;
an electrode within each of the three or more fluid chambers; and
three or more nanopores in the branched nanochannel;
wherein two or more nanopores are adjacent to each other on different branches of the branched nanochannel;
applying an electric potential across each pair of electrodes in the fluid chambers;
wherein two or more different electric potentials are applied on the two or more nanopores adjacent to each other on different branches of the branched nanochannel;
measuring an electric current across each pair of electrodes in the fluid chambers; and
detecting the passage of nucleic acid through the nanopores as current blockage of the nanopores.

In one embodiment, the nucleic acid is single stranded or double stranded. In one embodiment, the nucleic acid is single stranded and is hybridized with a single stranded nucleic acid probe to form a double stranded region at a target location of the nucleic acid. In one embodiment, the nucleic acid probe is from 15 to 1000 nucleotides. In one embodiment, the current blockage comprises different steps for the single stranded nucleic acid and the double stranded region.

In one embodiment, the nucleic acid comprises an attachment at a target location of the nucleic acid. In one embodiment, the attachment is selected from protein, metal particles, inorganic particles, a nucleic acid fragment, a nucleic acid fragment with a protein, or a nucleic acid fragment with a particle. In one embodiment, the current blockage comprises different steps for the nucleic acid and the attachment.

In one embodiment, the electric potential is adjusted based on the measurement of an electrical current. In one embodiment, the two or more different electric potentials applied on the two or more adjacent nanopores on different branches of the branched nanochannel is adjusted based on the measurement of electrical currents across the adjacent nanopores. In one embodiment, the adjustment of the electrical potentials allows the nucleic acid to be sorted into different fluid chambers connected to different branches of the branched nanochannel.

In one embodiment, the nanopores have a diameter from 2 nm to 100 nm. In one embodiment, the nanopores have a diameter from 10 nm to 20 nm.

In one embodiment, the adjacent nanopores are from 0.5 µm to 10 µm apart. In one embodiment, the adjacent nanopores are from 1 µm to 3 µm apart.

In one embodiment, the nanochannel has a diameter from 50 nm to 1000 nm. In one embodiment, the nanochannel has a diameter from 200 nm to 400 nm. In one embodiment, the nanochannel has a length from 5 µm to 100 µm. In one embodiment, the nanochannel has a length from 10 µm to 30 µm.

In one aspect, provided herein is a method for fabricating a branched nanochannel device, comprising:
depositing an insulating layer on top of a substrate;
creating a branched wire on the insulating layer, wherein the branched wire comprises three or more branches and three or more notches on the branched wire, wherein two or more notches are adjacent to each other on different branches of the branched wire;

depositing an additional insulating layer on top of the branched wire; and removing the branched wire to form a branched nanochannel.

In one embodiment, the insulating layer is comprised of silicon oxide, silicon nitride, aluminum oxide, zirconia oxide, niobium oxide, boron nitride, indium phosphide, aluminum phosphide, or combinations thereof.

In one embodiment, the additional insulating layer is comprised of silicon oxide, silicon nitride, aluminum oxide, zirconia oxide, niobium oxide, boron nitride, indium phosphide, aluminum phosphide, or combinations thereof.

In one embodiment, the substrate is comprised of silicon, germanium, sapphire, gallium arsenide, indium phosphide, aluminum oxide, or combinations thereof.

In one embodiment, the branched wire on the insulating layer is created by a method comprising:

electrodepositing a metal wire into a template, wherein the metal wire comprises two or more metals or alloys;

dissolving the template;

creating notches by etching one of the metals or alloys in the metal wire;

collecting the metal wire; and dispersing the metal wire onto the insulating layer.

In one embodiment, the metal wire comprises a metal or alloy of elements selected from Cr, Mn, Ni, Fe, Co, Cu, Zn, Ga, Ge, Mo, Ru, Rh, Pd, Ag, Cd, In, Sn, Sb, Te, Re, Pt, Au, Pb, or Bi. In one embodiment, the metal wire comprises an alloy selected from NiFe, NiFeCo, NiFeCu, CoFeCu, NiZn, NiFeZn, CuZn, NiFePd, CuPd, or CuIn. In one embodiment, the metal wire comprises a NiFe alloy with Ni content between 20 to 100 wt % and Fe content between 0 to 80 wt %.

In one embodiment, the template is comprised of aluminum oxide, silicon oxide, or polycarbonate.

In one embodiment, the notches are created by etching one of the metals or alloys in the metal wire in a solution comprising nitric acid, sulfuric acid, phosphoric acid, chromium oxide, ferric chloride, potassium permanganate, citric acid, tartaric acid, or oxalic acid.

In another embodiment, the branched wire on the insulating layer is created by a method comprising:

depositing a branched first metal wire of a first material on the insulating layer;

depositing one or more metal wires of a second material on the insulating layer, wherein the second material is different from the first material and the one or more metal wires of the second material overlap with the branched first metal wire of the first material at locations where the notches are to be placed;

inter-diffusing the second material into the first material at the locations of the overlaps by heating the substrate and wires to form a hybrid wire portion;

removing the one or more metal wires of the second material except for the locations of overlaps; and creating notches on the branched first metal wire of the first material by etching the hybrid wire portion at the locations of overlaps.

In one embodiment, the first material is selected from Cr, Mn, Ni, Fe, Co, Cu, Zn, Ga, Ge, Mo, Ru, Rh, Pd, Ag, Cd, In, Sn, Sb, Te, Re, Pt, Au, Pb, or Bi. In one embodiment, the second material is selected from Cr, Mn, Ni, Fe, Co, Cu, Zn, Ga, Ge, Mo, Ru, Rh, Pd, Ag, Cd, In, Sn, Sb, Te, Re, Pt, Au, Pb, or Bi. In one embodiment, the first material is selected from Ni, Cu, or Ag the second material is selected from Co, Fe, Zn, Ga, In, or Sn.

In one embodiment, the inter-diffusing is conducted at 100° C. to 800° C.

In one embodiment, the second metal wire of the second material is removed by etching in a solution comprising nitric acid, sulfuric acid, phosphoric acid, chromium oxide, ferric chloride, potassium permanganate, citric acid, tartaric acid, or oxalic acid.

In one embodiment, the notches are created by etching the locations of overlap on the branched first metal wire of the first material in a solution comprising nitric acid, sulfuric acid, phosphoric acid, chromium oxide, ferric chloride, potassium permanganate, citric acid, tartaric acid, or oxalic acid.

In one embodiment, the notches have a diameter from 2 nm to 100 nm. In one embodiment, the notches have a diameter from 10 nm to 20 nm.

In one embodiment, the adjacent notches are from 0.5 μm to 10 μm apart. In one embodiment, the adjacent notches are from 1 μm to 3 μm apart.

In one embodiment, the nanochannel has a diameter from 50 nm to 1000 nm. In one embodiment, the nanochannel has a diameter from 200 nm to 400 nm. In one embodiment, the nanochannel has a length from 5 μm to 100 μm. In one embodiment, the nanochannel has a length from 10 μm to 30 μm.

BRIEF DESCRIPTION OF THE DRAWINGS

The accompanying figures, which are incorporated in and constitute a part of this specification, illustrate several aspects described below.

DETAILED DESCRIPTION

Figure 1:
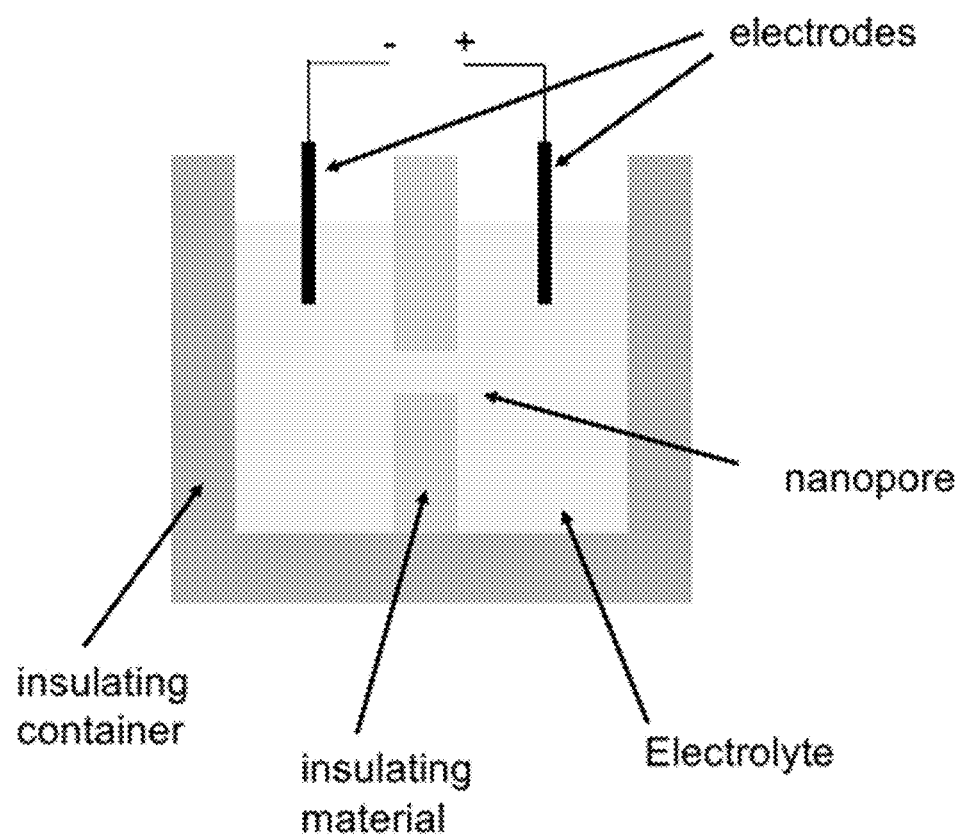
FIG. 1 shows a schematic of a prior art device for detection of nucleic acids. The two electrolytes are separated by an insulating membrane with a small pore on it, and the conductance between the two electrolytes are determined by the conductance across the pore, which is related to the area (size) of the pore. This conductance can be measured as the electric current between a pair of electrodes placed in the two electrolytes.

Disclosed herein are branched nanochannel devices and methods for the detection and/or sorting of nucleic acids. Further disclosed are methods for the fabrication of branched nanochannel devices.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used herein, the article "a," "an," and "the" means "at least one," unless the context in which the article is used clearly indicates otherwise.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22:1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" or "hybridizes" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "target" refers to a molecule that has an affinity for a given probe. Targets may be naturally-occurring or man-made molecules. Also, they can be employed in their unaltered state or as aggregates with other species.

As used throughout, by a "subject" (or a "host") is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

The term "adjacent" as used herein means, near, next to or adjoining. In some embodiments, the adjacent nanopores are in close physical proximity, but are located in different nanochannels (for example, nanopores 2 and 3 in FIG. 3). In one embodiment, the distance between the adjacent nanopores can be from 0.5 µm to 10 µm.

The term "about" as used herein when referring to a measurable value such as an amount, a percentage, and the like, is meant to encompass variations of ±20%, ±10%, ±5%, or ±1% from the measurable value.

Branched Nanochannel Devices

In one aspect, disclosed herein is a device comprising:
a branched nanochannel;
three or more fluid chambers connected by the branched nanochannel; and
three or more nanopores in the branched nanochannel;
wherein two or more nanopores are adjacent to each other on different branches of the branched nanochannel.

In one embodiment, the device further comprises an electrode within each of the three or more fluid chambers.

In some embodiments, the nanopore (or nanogate) can have a cross section shape that is round, square, or can be an irregular shape. The diameter of the cross section of the nanopore can be, for example, from 2 nm to 50 nm in diameter. In one embodiment, the cross section of the nanopore can range from 2 nm×2 nm to 50 nm×50 nm. In one embodiment, the area of the cross section of the nanopore can be from 4 to 2500 $nm^2$. In one embodiment, the nanopores are dimensioned to allow a linearized nucleic acid to pass through the nanopores. In one embodiment, the nanopores have a diameter from 2 nm to 100 nm. In one embodiment, the nanopores have a diameter from 10 nm to 20 nm. In one embodiment, the nanopore is from 5 nm to 20 nm in diameter.

In one embodiment, the length of the nanopore can be from 10 nm to 300 nm. In a preferred embodiment, the length of the nanopore can be from 50 nm to 200 nm. In a more preferred embodiment, the length of the nanopore can be from 100 nm to 200 nm.

In one embodiment, the distance between the adjacent nanopores (for example, nanopores 2 and 3 in FIG. 3) can be from 0.5 µm to 10 µm. In a preferred embodiment, the distance between the adjacent nanopores can be from 1 µm to 5 µm. In a more preferred embodiment, the distance between the adjacent nanopores can be from 1 µm to 3 µm.

In one embodiment, the nanochannel can have a cross section shape that is round, square, or can be an irregular shape. The diameter of the cross section of the nanochannel can be, for example, from 50 nm to 1000 nm in diameter. In one embodiment, the cross section of the nanochannel can range from 50 nm×50 nm to 1000 nm×1000 nm. In one embodiment, the area of the cross section of the nanopore can be from 2,500 to 1,000,000 $nm^2$. In one embodiment, the nanochannel has a diameter from 50 nm to 1000 nm. In one embodiment, the nanochannel is from 100 nm-500 nm in diameter. In one embodiment, the nanochannel has a diameter from 200 nm to 400 nm.

In one embodiment, the length of the nanochannel can be from 5 µm to 100 µm. In a preferred embodiment, the length of the nanochannel can be from 10 µm to 50 µm. In a more preferred embodiment, the length of the nanochannel can be from 10 µm to 30 µm.

In one embodiment, the nanopore and nanochannel are aligned. In one embodiment, the nanopore is located inside the nanochannel. In one embodiment, the nanochannel surrounds the nanopore.

In one embodiment, the fluid chamber can have a cross section shape that is round, square, or can be an irregular shape. In one embodiment, the cross section of the fluid chamber can range from (2 µm to 1000 µm)×(1 µm to 10 µm). In one embodiment, the area of the cross section of the nanopore can be from 4 to 10,000 $µm^2$. In a preferred embodiment, the cross section of the fluid chamber is from (2 µm to 100 µm)×(1 µm to 5 µm). In a more preferred embodiment, the cross section of the fluid chamber is from (5 µm to 10 µm)×(2 µm to 3 µm). In a particular embodiment, the fluid chamber is 5 µm×2 µm.

In one embodiment, the fluid chamber and nanochannel are aligned. In one embodiment, the nanochannel is connected to inside the fluid chamber.

In one embodiment, the insulating layer (or insulating material) is comprised of an oxide, nitride, phosphide, or ceramic. Some nonlimiting examples of materials used for the insulating layer include, silicon oxide, silicon nitride, aluminum oxide, zirconia oxide, niobium oxide, boron nitride, indium phosphide, aluminum phosphide, and the like.

In one embodiment, the substrate has a flat surface. In one embodiment, the substrate has is selected from, for example, wafers such as silicon, germanium, sapphire, gallium arsenide, indium phosphide, aluminum oxide, and the like. In one embodiment, the substrate is composed of multiple layers of materials. In one embodiment, the insulating layer is on top of the substrate.

Methods of Nucleic Acid Detection and Sorting

In another aspect, disclosed herein is a method for detecting a nucleic acid, comprising: introducing a nucleic acid into a fluid chamber of a device, wherein the device comprises:
a branched nanochannel;
three or more fluid chambers connected by the branched nanochannel;
an electrode within each of the three or more fluid chambers; and
three or more nanopores in the branched nanochannel;
wherein two or more nanopores are adjacent to each other on different branches of the branched nanochannel;
applying an electric potential across each pair of electrodes in the fluid chambers;
wherein two or more different electric potentials are applied on the two or more nanopores adjacent to each other on different branches of the branched nanochannel;

measuring an electric current across each pair of electrodes in the fluid chambers; and detecting the passage of nucleic acid through the nanopores as current blockage of the nanopores.

In one embodiment, the nucleic acid is single stranded or double stranded. In one embodiment, the nucleic acid is single stranded and is hybridized with a single stranded nucleic acid probe to form a double stranded region at a target location of the nucleic acid. In one embodiment, the nucleic acid probe is from 15 to 1000 nucleotides. In one embodiment, the current blockage comprises different steps for the single stranded nucleic acid and the double stranded region.

In one embodiment, the nucleic acid comprises an attachment at a target location of the nucleic acid. In one embodiment, the attachment is selected from protein, metal particles, inorganic particles, a nucleic acid fragment, a nucleic acid fragment with a protein, or a nucleic acid fragment with a particle. In one embodiment, the current blockage comprises different steps for the nucleic acid and the attachment.

In one embodiment, the nanopores have a diameter from 2 nm to 100 nm. In one embodiment, the nanopores have a diameter from 10 nm to 20 nm.

In one embodiment, the adjacent nanopores are from 0.5 μm to 10 μm apart. In one embodiment, the adjacent nanopores are from 1 μm to 3 μm apart.

In one embodiment, the nanochannel has a diameter from 50 nm to 1000 nm. In one embodiment, the nanochannel has a diameter from 200 nm to 400 nm. In one embodiment, the nanochannel has a length from 5 μm to 100 μm. In one embodiment, the nanochannel has a length from 10 μm to 30 μm.

In another aspect, disclosed herein is a method for sorting a nucleic acid, comprising: introducing a nucleic acid into a fluid chamber of a device, wherein the device comprises:
 a branched nanochannel;
 three or more fluid chambers connected by the branched nanochannel;
 an electrode within each of the three or more fluid chambers; and
 three or more nanopores in the branched nanochannel;
 wherein two or more nanopores are adjacent to each other on different branches of the branched nanochannel;
 applying an electric potential across each pair of electrodes in the fluid chambers;
 wherein two or more different electric potentials are applied on the two or more nanopores adjacent to each other on different branches of the branched nanochannel;
 measuring an electric current across each pair of electrodes in the fluid chambers; and
 sorting the nucleic acid into a fluid chamber.

In one embodiment, the electric potential is adjusted based on the measurement of an electrical current. In one embodiment, the two or more different electric potentials applied on the two or more adjacent nanopores on different branches of the branched nanochannel is adjusted based on the measurement of electrical currents across the adjacent nanopores. In one embodiment, the adjustment of the electrical potentials allows the nucleic acid to be sorted into different fluid chambers connected to different branches of the branched nanochannel.

Methods of Device Fabrication

In one aspect, provided herein is a method for fabricating a branched nanochannel device, comprising:
 depositing an insulating layer on top of a substrate;
 creating a branched wire on the insulating layer, wherein the branched wire comprises three or more branches and three or more notches on the branched wire, wherein two or more notches are adjacent to each other on different branches of the branched wire;
 depositing an additional insulating layer on top of the branched wire; and
 removing the branched wire to form a branched nanochannel.

In one embodiment, the insulating layer is comprised of silicon oxide, silicon nitride, aluminum oxide, zirconia oxide, niobium oxide, boron nitride, indium phosphide, aluminum phosphide, or combinations thereof.

In one embodiment, the additional insulating layer is comprised of silicon oxide, silicon nitride, aluminum oxide, zirconia oxide, niobium oxide, boron nitride, indium phosphide, aluminum phosphide, or combinations thereof.

In one embodiment, the substrate is comprised of silicon, germanium, sapphire, gallium arsenide, indium phosphide, aluminum oxide, or combinations thereof.

In one aspect, provided herein is a method for fabricating a branched nanochannel device, comprising:
 depositing an insulating layer on top of a substrate;
 creating a branched wire on the insulating layer;
 wherein the branched wire comprises three or more branches and three or more notches on the branched wire, wherein two or more notches are adjacent to each other on different branches of the branched wire;
 wherein the branched wire is created by a method comprising:
  electrodepositing a metal wire into a template, wherein the metal wire comprises two or more metals or alloys;
  dissolving the template;
  creating notches by etching one of the metals or alloys in the metal wire;
  collecting the metal wire; and
  dispersing the metal wire onto the insulating layer;
 depositing an additional insulating layer on top of the branched wire; and
 removing the branched wire to form a branched nanochannel.

In one embodiment, the metal wire comprises a metal or alloy of elements selected from Cr, Mn, Ni, Fe, Co, Cu, Zn, Ga, Ge, Mo, Ru, Rh, Pd, Ag, Cd, In, Sn, Sb, Te, Re, Pt, Au, Pb, or Bi. In one embodiment, the metal wire comprises an alloy selected from NiFe, NiFeCo, NiFeCu, CoFeCu, NiZn, NiFeZn, CuZn, NiFePd, CuPd, or CuIn. In one embodiment, the metal wire comprises a NiFe alloy with Ni content between 20 to 100 wt % and Fe content between 0 to 80 wt %.

In one embodiment, the template is comprised of aluminum oxide, silicon oxide, or polycarbonate.

In one embodiment, the notches are created by etching one of the metals or alloys in the metal wire in a solution comprising nitric acid, sulfuric acid, phosphoric acid, chromium oxide, ferric chloride, potassium permanganate, citric acid, tartaric acid, or oxalic acid.

In one aspect, provided herein is a method for fabricating a branched nanochannel device, comprising:
 depositing an insulating layer on top of a substrate;
 creating a branched wire on the insulating layer;
 wherein the branched wire comprises three or more branches and three or more notches on the branched wire, wherein two or more notches are adjacent to each other on different branches of the branched wire;

wherein the branched wire is created by a method comprising:
depositing a branched first metal wire of a first material on the insulating layer;
depositing one or more metal wires of a second material on the insulating layer, wherein the second material is different from the first material and the one or more metal wires of the second material overlap with the branched first metal wire of the first material at locations where the notches are to be placed;
inter-diffusing the second material into the first material at the locations of the overlaps by heating the substrate and wires to form a hybrid wire portion;
removing the one or more metal wires of the second material except for the locations of overlaps; and
creating notches on the branched first metal wire of the first material by etching the hybrid wire portion at the locations of overlaps;
depositing an additional insulating layer on top of the branched wire; and
removing the branched wire to form a branched nanochannel.

In one embodiment, the first material is selected from Cr, Mn, Ni, Fe, Co, Cu, Zn, Ga, Ge, Mo, Ru, Rh, Pd, Ag, Cd, In, Sn, Sb, Te, Re, Pt, Au, Pb, or Bi. In one embodiment, the second material is selected from Cr, Mn, Ni, Fe, Co, Cu, Zn, Ga, Ge, Mo, Ru, Rh, Pd, Ag, Cd, In, Sn, Sb, Te, Re, Pt, Au, Pb, or Bi. In one embodiment, the first material is selected from Ni, Cu, or Ag the second material is selected from Co, Fe, Zn, Ga, In, or Sn.

In one embodiment, the metal wires of the first and second materials can be deposited with methods selected from sputtering, physical vapor deposition, evaporation, chemical vapor deposition, atomic layer deposition, electrodeposition and the combination of such. In one embodiment, the metal wires are formed using methods selected from optical lithography, UV lithography, electron beam lithography, assembly, lift off, sputter etching, chemical etching, plasma etching.

In one embodiment, the inter-diffusing is conducted at 100° C. to 800° C.

In one embodiment, the second metal wire of the second material is removed by etching in a solution comprising nitric acid, sulfuric acid, phosphoric acid, chromium oxide, ferric chloride, potassium permanganate, citric acid, tartaric acid, or oxalic acid.

In one embodiment, the notches are created by etching the locations of overlap on the branched first metal wire of the first material in a solution comprising nitric acid, sulfuric acid, phosphoric acid, chromium oxide, ferric chloride, potassium permanganate, citric acid, tartaric acid, or oxalic acid.

In one embodiment, the notches have a diameter from 2 nm to 100 nm. In one embodiment, the notches have a diameter from 10 nm to 20 nm.

In one embodiment, the adjacent notches are from 0.5 μm to 10 μm apart. In one embodiment, the adjacent notches are from 1 μm to 3 μm apart.

In one embodiment, the nanochannel has a diameter from 50 nm to 1000 nm. In one embodiment, the nanochannel has a diameter from 200 nm to 400 nm. In one embodiment, the nanochannel has a length from 5 μm to 100 μm. In one embodiment, the nanochannel has a length from 10 μm to 30 μm.

EXAMPLES

The following examples are set forth below to illustrate the devices, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1

Branched Nanochannel Devices

Figure 2:
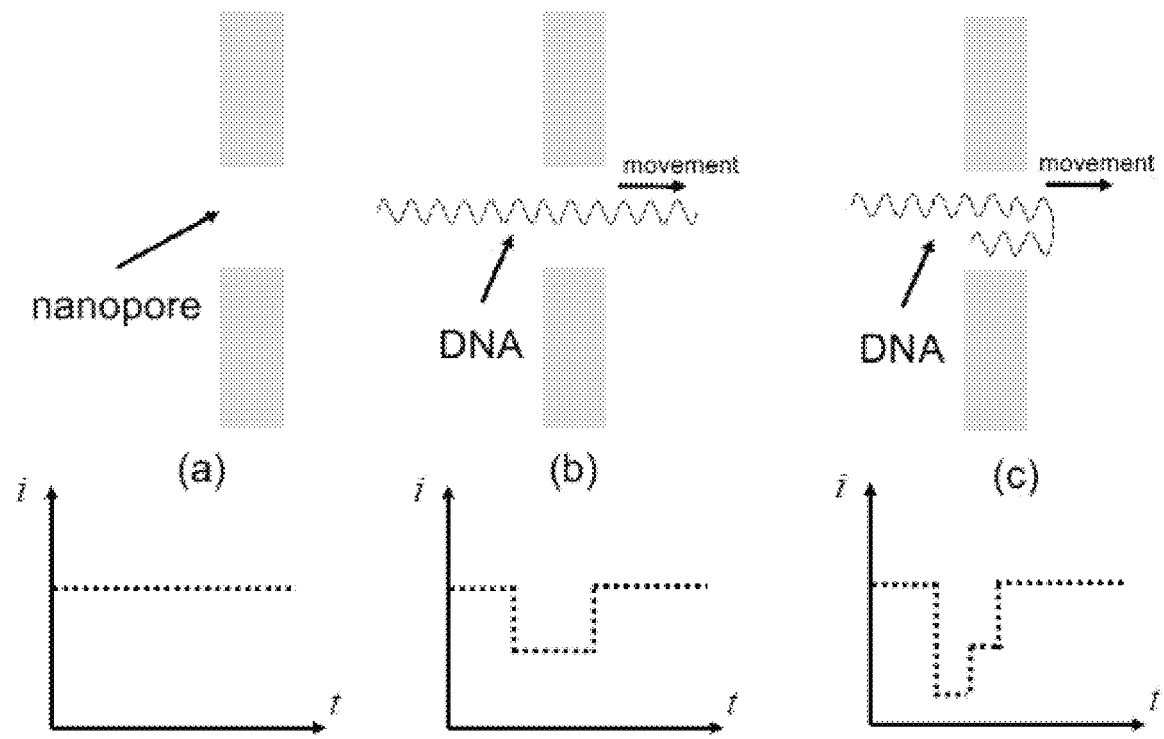
FIG. 2 shows a schematic of the prior art for the detection of a nucleic acid through a nanopore. (a) The current is measured across a nanopore between two electrodes. (b) The current across a nanopore is blocked by a strand of DNA when it is passing through the nanopore. The DNA is passing across the pore because of the electrophoretic force on the negatively charged DNA molecule. The current blockage is observed when the pore is small, for example, under 20 nm in diameter. (c) The configuration of DNA when it passes across the pore can be differentiated. A deeper current blockage is typically observed when a folded DNA pass through because of the larger blockage of the pore.

This example discloses various types of branched nanochannel devices. Regarding the background of the invention, when two electrolytes are separated by an insulating membrane with a small pore on it, the conductance between the two electrolytes are determined by the conductance across the pore, which is related to the area (size) of the pore. This conductance can be measured as the electric current between a pair of electrodes placed in the two electrolytes (FIG. 1). The electrolyte can be for example, potassium chloride. Further, detection of DNA molecules through a nanopore (or nanogate) is shown according to FIG. 2. The current measured across a nanopore between two electrodes (FIG. 2a). The current across a nanopore is blocked by a strand of DNA when it is passing through the nanopore. The DNA is passing across the pore because of the electrophoretic force on the negatively charged DNA molecule. The current blockage is observed when the pore is small, for example, under 20 nm in diameter (FIG. 2b). The configuration of DNA when it passes across the pore can be differentiated. A deeper current blockage is typically observed when a folded DNA pass through because of the larger (FIG. 2c).

Figure 3:
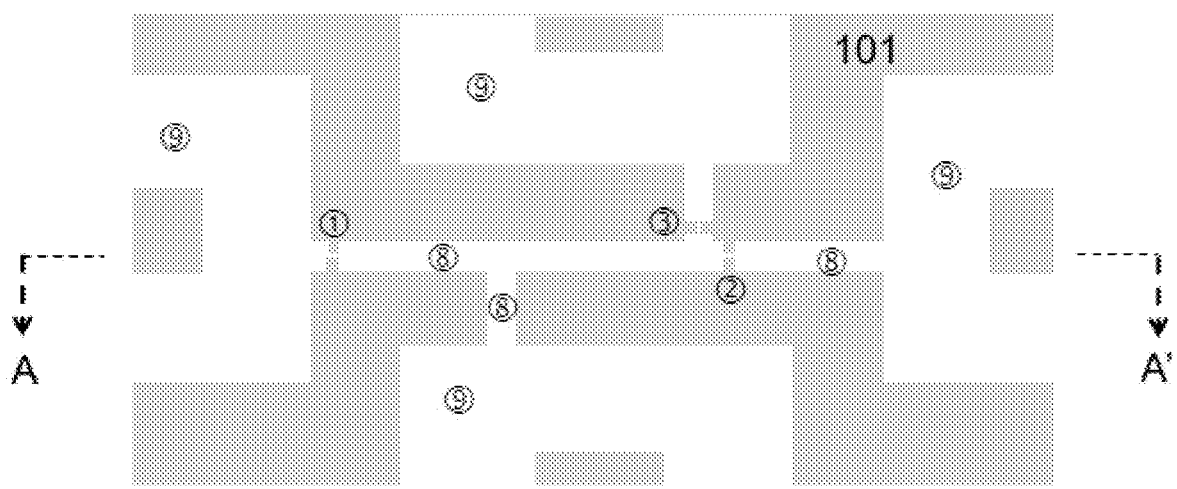
FIG. 3 shows an illustration of a branched nanochannel device. (a) View of the branched nanochannel device from the top. (b) Cross-sectional view of the branched nanochannel device.
Figure 3:
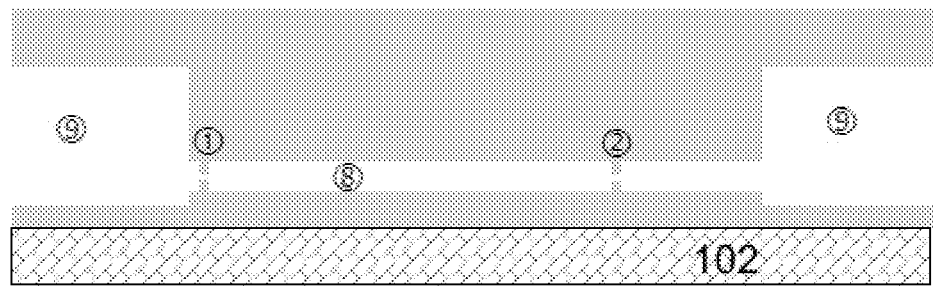

An example of a branched nanochannel device according to the invention is shown in FIG. 3. The insulating layer 101 is supported on top of a substrate 102. The substrate 102 can be for example, silicon, germanium, sapphire, oxides, and the like. The device has nanochannels 8 which connect the fluid chambers 9 (fluid chambers can also be referred to as microfluidic channels as well). The device has nanopores 1, 2, and 3 in the nanochannels 8. The device has two nanopores 2 and 3 that are adjacent to each other. In some embodiments, there can be additional nanochannels 8, nanopores, and fluid chambers 9. The fluid chambers 9 can be of any shape that allows fluid to pass through to the nanochannels 8. The nanochannels 8 can have different shapes (for example, can be curved) and do not have to be straight.

Figure 4:
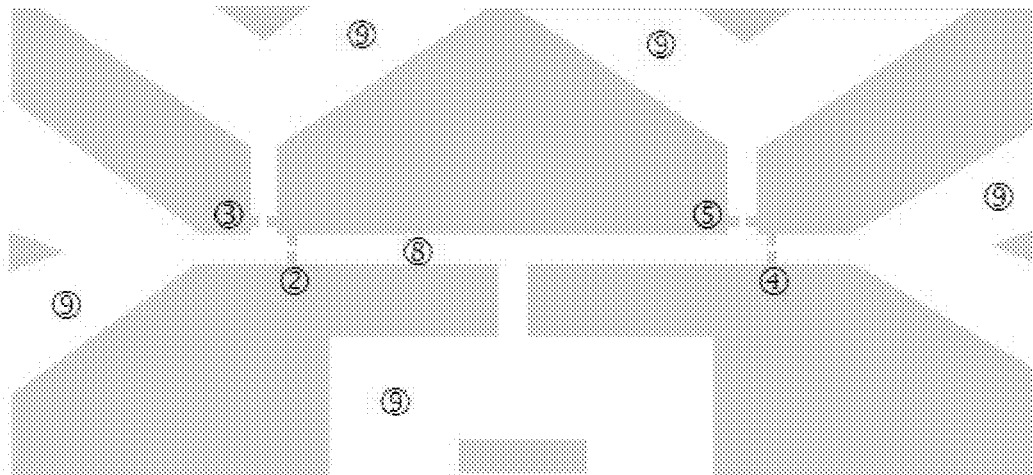
FIG. 4 shows an illustration of a branched nanochannel device with an increased number of nanopores. The branched nanochannel device is viewed from the top.

Another example of a branched nanochannel device according to the invention is shown in FIG. 4. FIG. 4 shows the top down view of the device. The device has nanochannels 8 which connect the fluid chambers 9. The device has nanopores 2, 3, 4, and 5 in the nanochannels 8. The device has at least two nanopores 2 and 3 that are adjacent to each other. In this example, the device can comprise an additional pair of adjacent nanopores 4 and 5. In some embodiments, there can be additional nanochannels 8, nanopores, and fluid chambers 9. The fluid chambers 9 can be of any shape that allows fluid to pass through to the nanochannels 8. The nanochannels 8 can have different shapes (for example, can be curved) and do not have to be straight.

Figure 5:
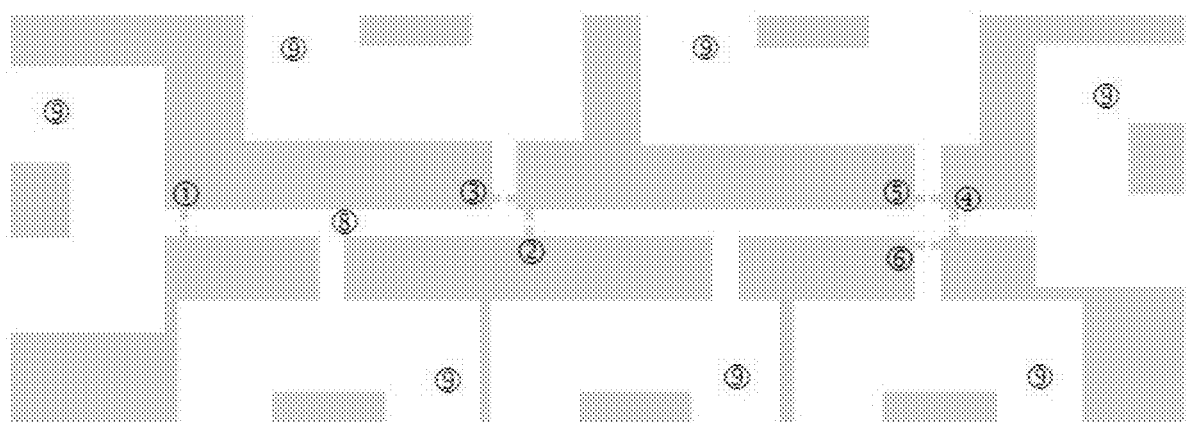
FIG. 5 shows another illustration of a branched nanochannel device with an additional increase in the number of nanopores. The branched nanochannel device is viewed from the top.

A further example of a branched nanochannel device according to the invention is shown in FIG. 5. FIG. 5 shows the top down view of the device. The device has nanochannels 8 which connect the fluid chambers 9. The device has nanopores 1, 2, 3, 4, 5, and 6 in the nanochannels 8. The device has at least two nanopores 2 and 3 that are adjacent to each other. In this example, the device can comprise an additional number of nanopores 4, 5, and 6, where the additional nanopores are optionally adjacent to one another. In some embodiments, there can be additional nanochannels 8, nanopores, and fluid chambers 9. The fluid chambers 9 can be of any shape that allows fluid to pass through to the nanochannels 8. The nanochannels 8 can have different shapes (for example, can be curved) and do not have to be straight.

Figure 6:
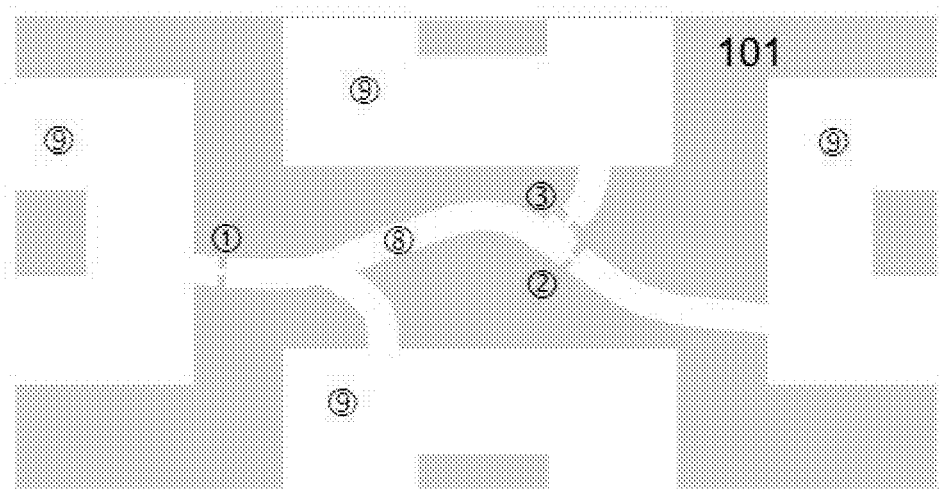
FIG. 6 shows an illustration of a branched nanochannel device where the nanochannel is curved, instead of straight. The branched nanochannel device is viewed from the top.

An example of a branched nanochannel device according to the invention is shown in FIG. 6. FIG. 6 shows the top down view of the device. The device has nanochannels 8 which connect the fluid chambers 9. The device has nanopores 1, 2, and 3 in the nanochannels 8. The device has at least two nanopores 2 and 3 that are adjacent to each other. In some embodiments, there can be additional nanochannels 8, nanopores, and fluid chambers 9. The fluid chambers 9 can be of any shape that allows fluid to pass through to the nanochannels 8. The nanochannels 8 can have different shapes (for example, can be curved, as shown in FIG. 6) and do not have to be straight. The nanochannels and nanopore are present in an insulating layer 101.

Figure 7:
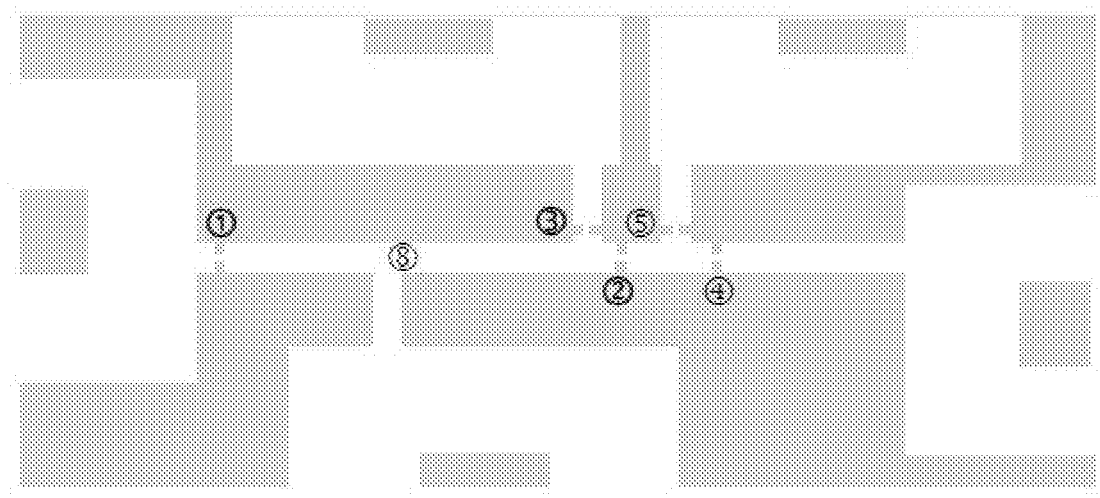
FIG. 7 shows another illustration of a branched nanochannel device where the nanopore locations have been moved in close proximity. The branched nanochannel device is viewed from the top.

Another example of a branched nanochannel device according to the invention is shown in FIG. 7. FIG. 7 shows the top down view of the device. The device has nanochannels 8 which connect the fluid chambers 9. The device has nanopores 1, 2, 3, 4, and 5 in the nanochannels 8. The device has at least two nanopores 2 and 3 that are adjacent to each other. In this example, the device can comprise an additional pair of adjacent nanopores 4 and 5. In some embodiments, there can be additional nanochannels 8, nanopores, and fluid chambers 9. The fluid chambers 9 can be of any shape that allows fluid to pass through to the nanochannels 8. The nanochannels 8 can have different shapes (for example, can be curved) and do not have to be straight.

Example 2

Methods for Detecting Nucleic Acids

This example discloses various methods for detection and/or sorting of nucleic acids using the branched nanochannel devices disclosed herein.

Figure 8:
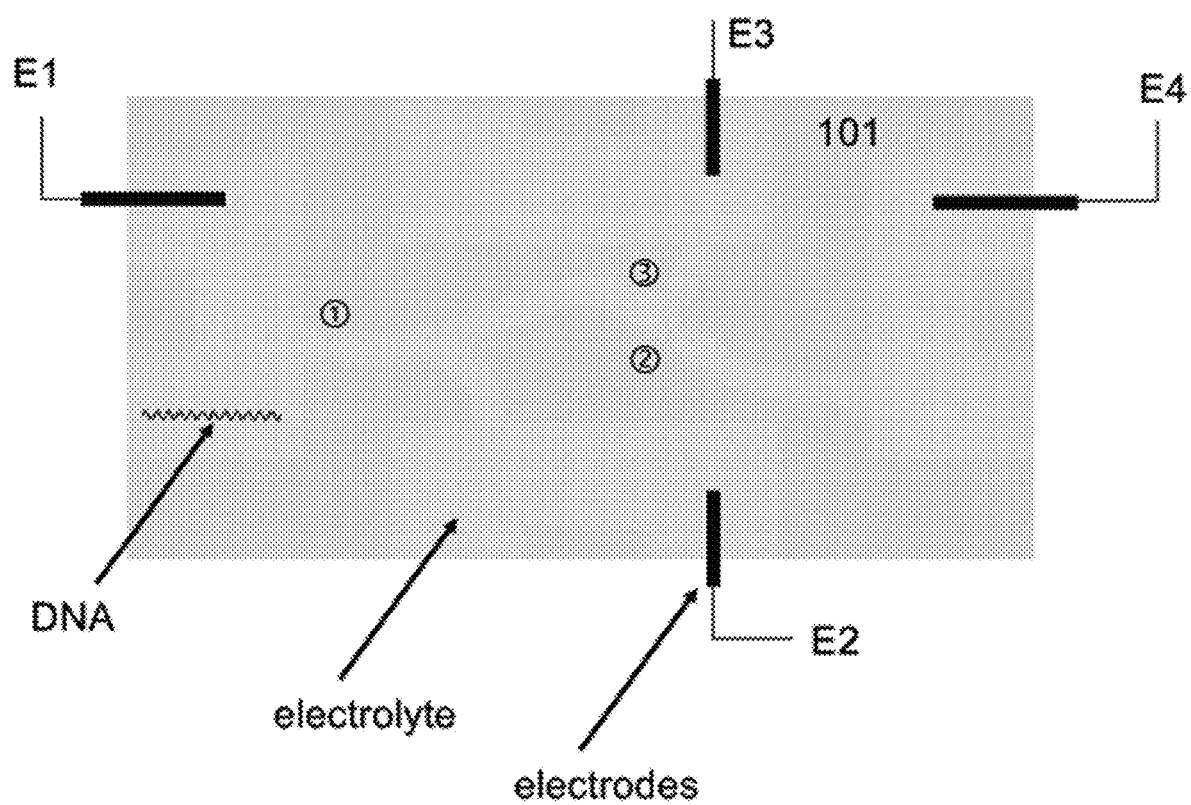
FIG. 8 shows an illustration of a branched nanochannel device where the electrodes can be seen in each fluid chamber. The DNA is introduced in one compartment and is pulled through the nanopores based on the different voltages applied to the four electrodes. The branched nanochannel device is viewed from the top.

As shown in FIG. 8, a branched nanochannel device is used to detect a nucleic acid. FIG. 8 shows the top down view of the device. The device has nanochannels which connect the fluid chambers. The device has nanopores 1, 2, and 3 in the nanochannels. The device has at least two nanopores 2 and 3 that are adjacent to each other. In some embodiments, there can be additional nanochannels, nanopores, and fluid chambers. The fluid chambers can be of any shape that allows fluid to pass through to the nanochannels. The nanochannels can have different shapes (for example, can be curved, as shown in FIG. 8) and do not have to be straight. The nanochannels and nanopore are present in an insulating layer 101.

An electrode is present in each of the fluid chambers. The four electrodes (E1, E2, E3, and E4) are controlled separately, and can have four different voltages.

In this particular example in FIG. 8, E1 is at the lowest potential. E2 is more positive than E1, and E3 and E4 are more positive than E2. E2−E1=0–2 V, preferably, 50–800 mV. This is the voltage applied on nanogate #1. E3−E2=0–2 V, preferably, 50–800 mV. This is the voltage applied on nanogate #3. E4−E2=0–2 V, preferably, 50–800 mV. This is the voltage applied on nanogate #2.

The nucleic acid (DNA) to be analyzed is introduced in the fluid chamber with electrode E1. The negatively charged DNA is then pulled through the nanopore 1.

Figure 9:
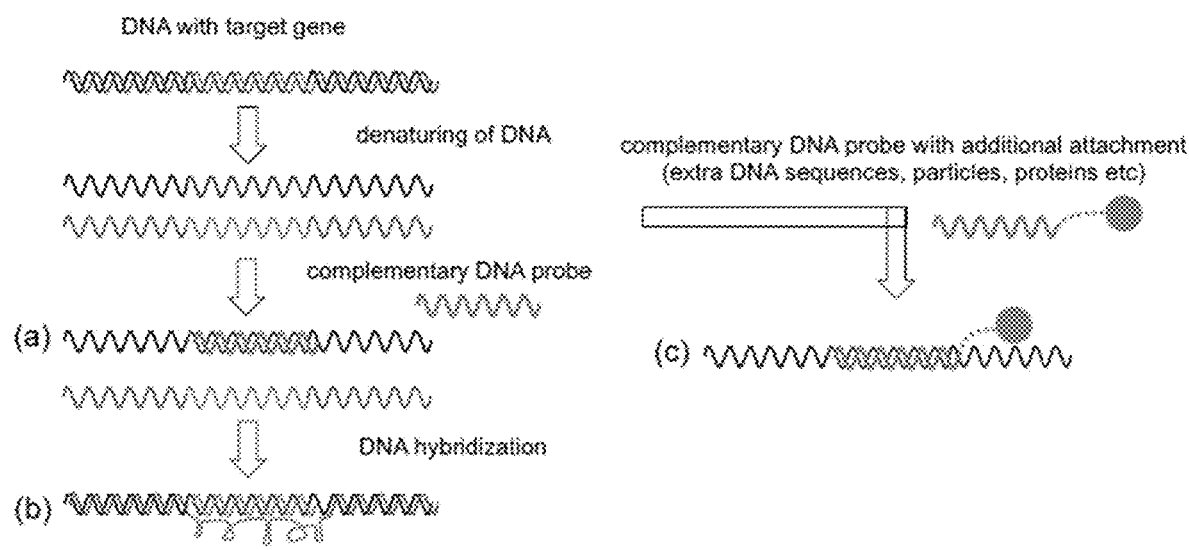
FIG. 9 shows a schematic of the method for the detection of nucleic acid. (a) The DNA is denatured, and a complementary probe is added. (b) The complementary probe binds to and hybridizes with the target DNA sequence. (c) In addition, a complementary DNA probe can have an additional attachment (for example, an extra DAN sequence, particles, proteins, etc.). The extra attachment can help provide even more blockage and more contrast for detection of the nucleic acid.

As shown in FIG. 9, DNA strands that are recognized by a nucleic acid probe to a target gene can be differentiated from the DNA strands without the target gene because this creates a deeper current blockage as the DNA passes through a nanopore. The nucleic acid probe can be a single stranded nucleic acid only, or can have attachment selected from protein, particles, polymers, and the combination of such. The voltages on nanopores 2 and 3 are controlled by E3−E2 and E4−E2 during the detection of genes on DNA and they can be used to pull the DNA to one of the two nanopores, 2 or 3, based on the detection of the genes.

Another embodiment uses the device in FIG. 7 to sort the nucleic acid. In this embodiment, the voltages on nanopores 4 and 5 are controlled based on the detection of genes on nanopore 2. The nucleic acid is thus pulled into one of the two nanopores 4 or 5 based on the detection of genes.

Yet another embodiment uses the device in FIG. 5 to sort the nucleic acid. In this embodiment, the voltages on nanopores 4, 5, 6 are controlled based on the detection of genes on nanopore 2. The nucleic acid is thus pulled into one of the three nanopores 4 or 5 or 6 based on the detection of genes.

Figure 10:
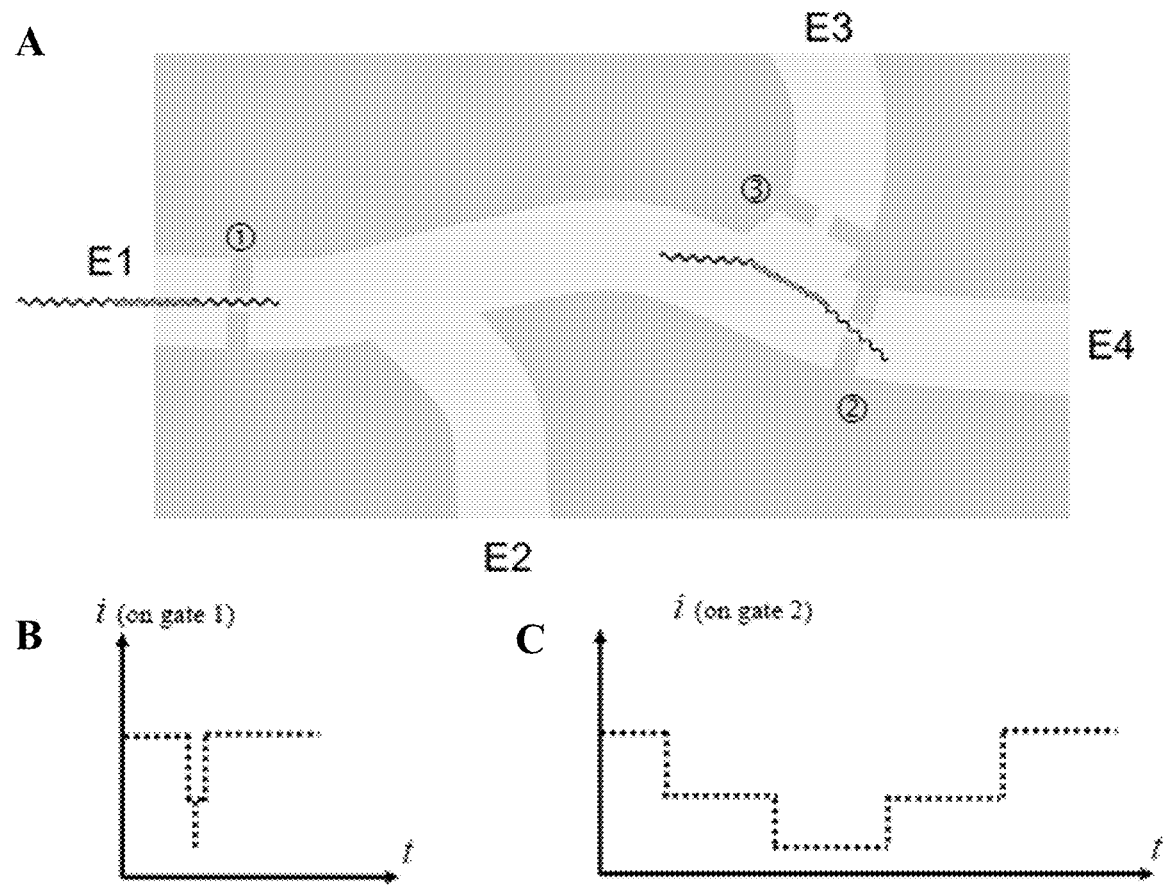
FIG. 10 shows an illustration of a branched nanochannel device where the nanochannel is curved, and the DNA is being pulled though the nanopores. (a) The branched nanochannel device is viewed from the top. (b) The current blockage of the DNA passing through the nanopore is shown. The current depends on the cross section of the DNA and the speed it passes through the nanopore. (c) The current blockage of the DNA passing through the nanopore is shown at a slower speed. The speed at which the DNA passes through the pore needs to allow for the differentiation of the deeper current blockage by the double-stranded region containing the probe hybridized to the target sequence.

As shown in FIG. 10a, the DNA passes though nanopore 1 under the electrophoretic force by the voltage bias $\Delta E1E2=E2-E1$. The frequency of this passage increases as the $\Delta E1E2$ increases. The speed of passage also depends on $\Delta E1E2$. The DNA then passes through nanopore 2 under the electrophoretic force by the voltage bias $\Delta E2E4=E4-E2$. The speed of passage is controlled by the competition between $\Delta E2E4$ and $\Delta E2E3$. The voltage $\Delta E2E3$ on nanopore 3 also attracts DNA and slows down the passage of the DNA on nanopore 2. DNA can also pass on nanopore 3 if the electrophoretic force by nanopore $\Delta E2E3$ is stronger. As seen in FIGS. 10b and 10c, the current blockage depends on the cross section of the DNA. The genes on the DNA can be detected after labelling. The relative location of the genes on the DNA can be detected. For example, as seen in FIG. 10c, the deeper current blockage in the middle of the whole blockage because the gene is in the middle of the DNA.

Figure 11:
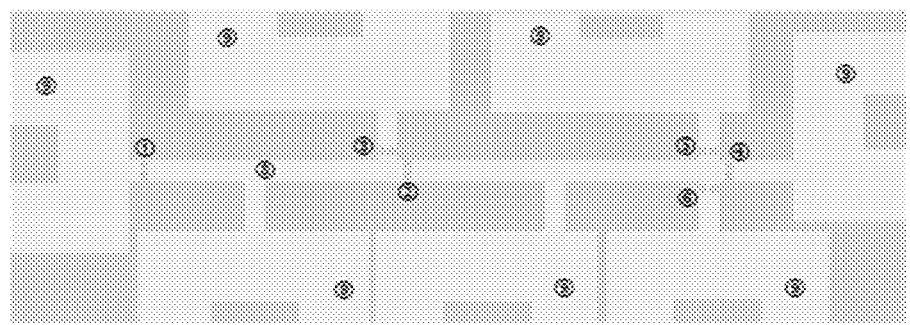
FIG. 11 shows an illustration of a branched nanochannel device with additional nanopores. The additional nanopores can allow for sorting of DNA into different branches based on gene detection results.

As shown in FIG. 11, a device can be used that has additional nanopores. Nanopores 2 and 3 can be used to detect the presence of the gene on the DNA. The voltage on nanopores 4, 5, and 6 can be controlled according to the detection results. The DNA can then be sorted into different branches of the branched nanochannel and fluid chambers based on the gene detection results. In this method, the DNA can be sorted by the presence (or absence) of the target gene of interest.

Example 3

Methods for Device Fabrication

This example discloses various methods for fabrication of the branched nanochannel devices disclosed herein.

Figure 12:
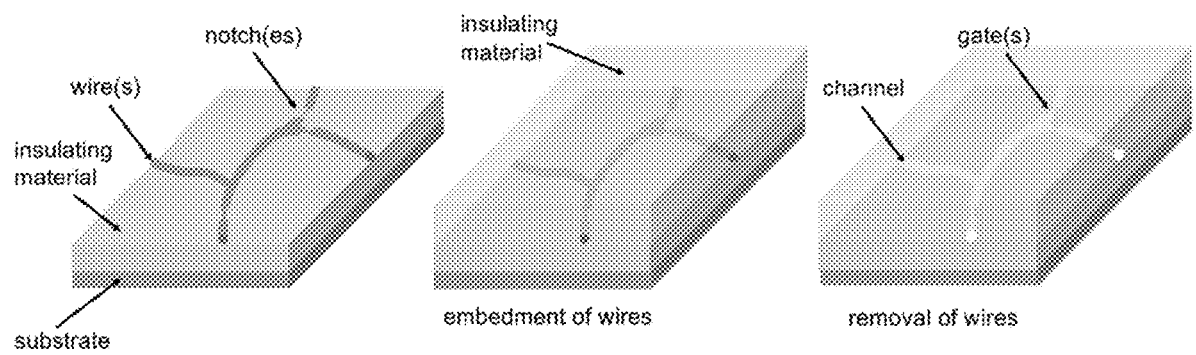
FIG. 12 shows a schematic of the method of fabrication of the branched nanochannel device. Wires with notches are fabricated, embedded into the insulating material, and then removed by etching.

FIG. 12 shows the subtractive etching of shape modulated wires to make channels with pores. The branched nanochannel device can be made by fabricating wires with notches, followed by embedding the wires in the insulating material, and subtractively etching (removing) these wires. The channels are then created in the insulating materials by removing the wires. The nanogates (or nanopores) are created at the locations where the notches are located along the wires.

Figure 13:
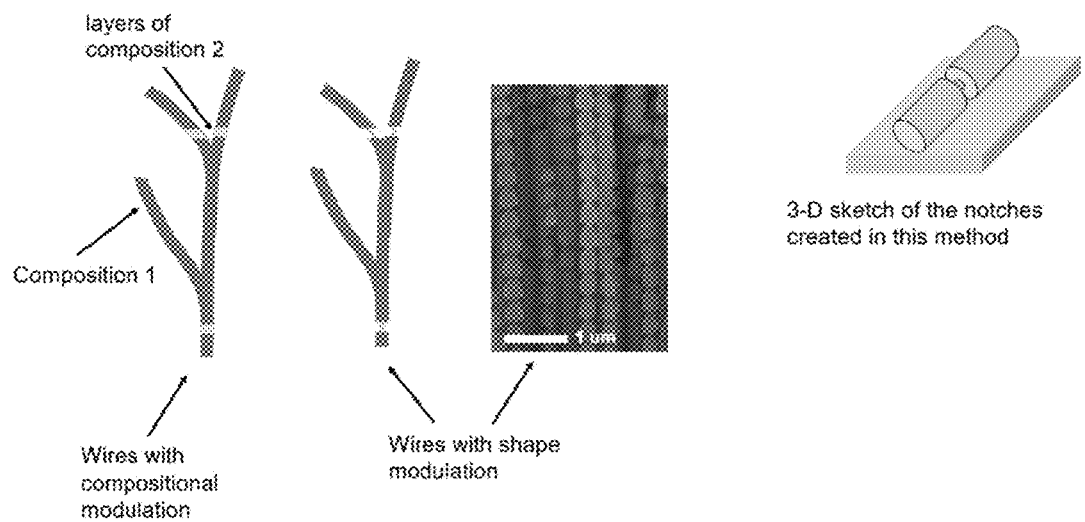
FIG. 13 shows a schematic of the fabrication of wires with notches using compositionally modulated wires. (a) Wires are created using different compositions (elements or alloys). (b) An electron micrograph of a notched wire is shown. (c) A 3-D sketch of the notches created by use of compositionally modulated wires.
Figure 14:
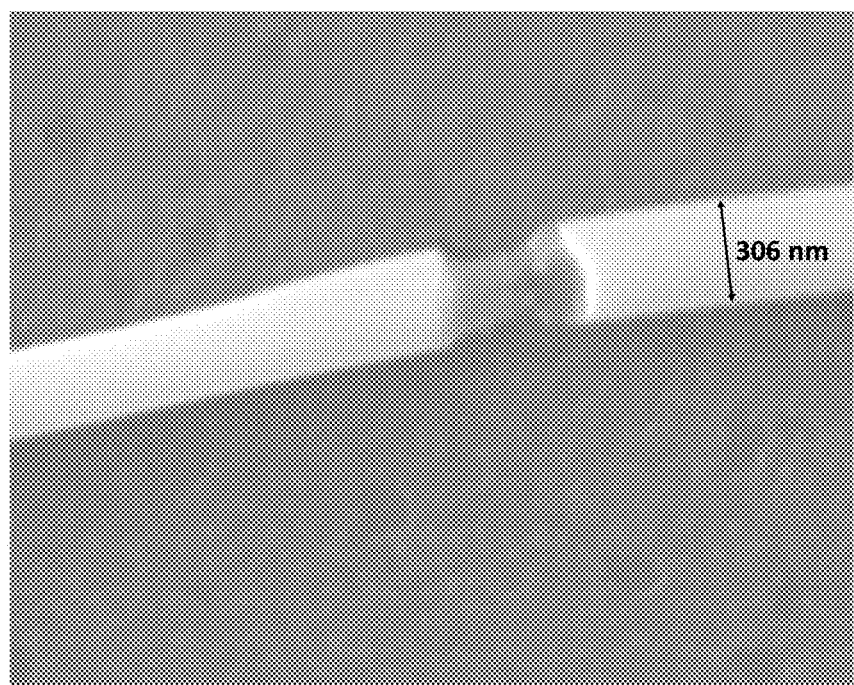
FIG. 14 shows a single nanowire electrodeposited with one compositional modulation, released from template, dispersed on a substrate, and then etched to create a narrower region. The width of the nanowire as seen in FIG. 14 is approximately 306 nm.

As shown in FIG. 13, the branched nanochannel device can be fabricated by use of compositionally modulated wires. The wires can be fabricated with electrodeposition. The wires comprise layers with different compositions (metals of alloys). The layers comprising the different compositions can be electrodeposited with pulsed potential, pulsed current, or pulsed agitation. In one example, NiFe alloys wires are electrodeposited along with alloys of different compositions at different potentials. The layers with different compositions are etched differently with various etching chemistries. Layers with certain compositions are etched and preferably creating notches along the wires. In FIG. 14, a single nanowire electrodeposited with one compositional modulation, released from template, dispersed on a substrate, and then etched to create a narrower region is shown. The nanowire is then capped and etched to create the channel.

For the electrodeposition of the wires, a template is used. Example templates include aluminum oxide templates, diblock copolymer templates, or nuclear track etched templates. The template can also be fabricated in other ways to create branches. After the deposition of wires with modulated compositions in the template, the template is dissolved to release the wires. In another example, direct electrodeposition can be used to form free wires with modulated compositions, such as electrochemical 3-dimensional printing. The free wires can be etched such that one layer of the compositions are selectively etched to create notched regions along the wires. The wires with notches are collected in liquid solution and dispersed on insulating layer on the substrate.

Figure 15:
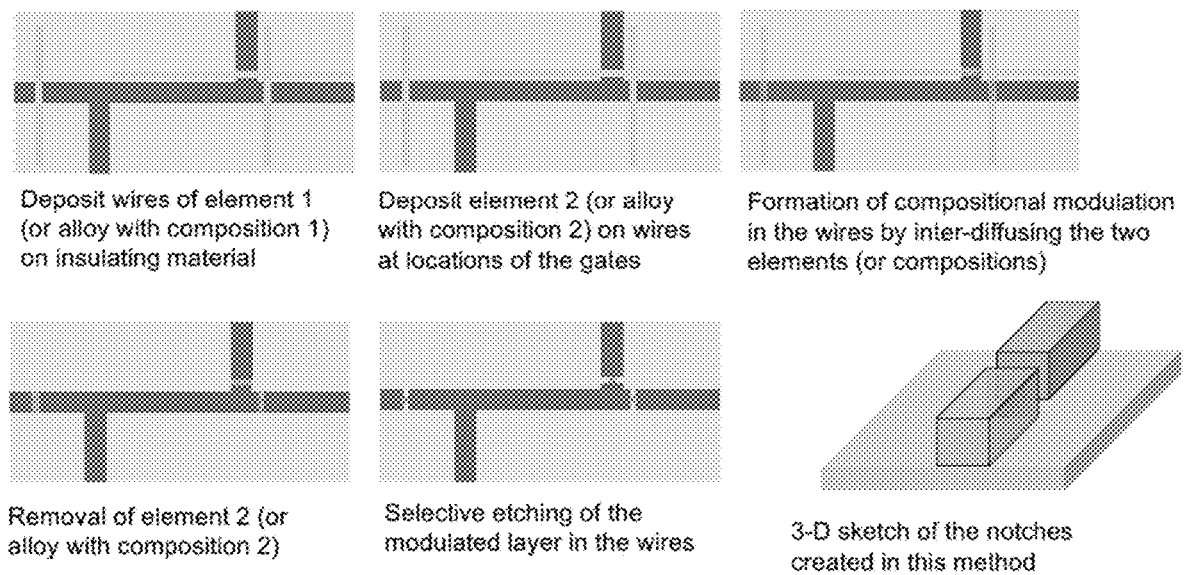
FIG. 15 shows a schematic of the fabrication of wires with notches using compositionally modulated wires. (a) Deposit wires of element 1 (or alloy with composition 1) on the insulating material. (b) Deposit element 2 (or alloy with composition 2) on the wires at the location the nanopores (nanogates). (c) The formation of compositional modulation in the wires occurs by inter-diffusion of the two elements (or alloys (compositions)). (d) Element 2 (or alloy with composition 2) is removed. (e) The selective etching of the modulated layer is performed to create the notches in the wire. (f) A 3-D sketch of the notches created by this process is shown.

The fabrication methods are further shown in FIG. 15. First, deposit wires of element 1 (or alloy with composition 1) on the insulating material. Second, deposit element 2 (or alloy with composition 2) on the wires at the location the nanopores (nanogates). Third, the formation of compositional modulation in the wires occurs by inter-diffusion of the two elements (or alloys (compositions)). Fourth, element 2 (or alloy with composition 2) is removed. Fifth, the selective etching of the modulated layer is performed to create the notches in the wire. As further shown in FIG. 15, a 3-D sketch of the notches created by this process is shown.

The formation of the compositional modulation in the wires can also be achieved by other methods, for example, inter-diffusion of material at high temperature, implantation, or direct deposition (bombarding) of the second material. The formation of wires can be achieved with processes such as deposition (PVD, sputtering, evaporation, electrodeposition, CVD), followed by lithography patterning, followed by etching (dry etching or wet etching), and followed by pattern removal. In addition, wires can be formed by lithography patterning followed by deposition (evaporation, electrodeposition), and followed by lift-off.

The fluid chambers (or microfluidic channels) can be formed by processes such as deposition of insulating materials, lithography patterning, etching of insulting materials, and bonding.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

I claim:

1. A method for detecting a nucleic acid, comprising:
   introducing a nucleic acid into a fluid chamber of a device, wherein the device comprises:
   a branched nanochannel;
   three or more fluid chambers connected by the branched nanochannel;
   a different electrode within each of the three or more fluid chambers; and
   three or more nanopores in the branched nanochannel;
   wherein two or more nanopores are adjacent to each other on different branches of the branched nanochannel;
   applying an electric potential across each pair of different electrodes in the three or more fluid chambers;
   wherein two or more different electric potentials are applied on the two or more nanopores adjacent to each other on different branches of the branched nanochannel;
   measuring an electric current across each pair of different electrodes in the fluid chambers; and
   detecting the passage of nucleic acid through the nanopores as current blockage of the nanopores.

2. The method of claim 1, wherein the nucleic acid is single stranded and is hybridized with a single stranded nucleic acid probe to form a double stranded region at a target location of the nucleic acid.

3. The method of claim 1, wherein the current blockage comprises different steps for the single stranded nucleic acid and the double stranded region.

4. The method of claim 1, wherein the nucleic acid comprises an attachment at a target location of the nucleic acid.

5. The method of claim 1, wherein the attachment is selected from a protein, metal particles, inorganic particles, a nucleic acid fragment, a nucleic acid fragment with a protein, or a nucleic acid fragment with a particle.

6. The method of claim 1, wherein the current blockage comprises different steps for the nucleic acid and the attachment.

7. The method of claim 1, wherein the nanopores are dimensioned to allow a linearized nucleic acid to pass through the nanopores.

8. The method of claim 1, wherein the nucleic acid is single stranded or double stranded.

9. The method of claim 2, wherein the nucleic acid probe is from 15 to 1000 nucleotides.

10. The method of claim 1, wherein the electric potential is adjusted based on the measurement of an electrical current.

11. The method of claim 1, wherein the two or more different electric potentials applied on the two or more nanopores adjacent to each other on different branches are adjusted based on the electrical current blockage measured across each pair of electrodes in the fluid chambers.

12. The method of claim 1, wherein the two or more different electric potentials applied on the two or more nanopores adjacent to each other on different branches act on the nucleic acid and control the passage of the nucleic acid.

13. The method of claim 1, wherein the two or more different electric potentials applied on the two or more nanopores adjacent to each other on different branches compete for and slow down the passage of the nucleic acid through one of the adjacent nanopores.

14. The method of claim 1, wherein the two or more different electric potentials applied on the two or more nanopores adjacent to each other on different branches comprise different steps and are adjusted to intercept and reverse the passage of the nucleic acid through one of the nanopores.

15. The method of claim 14, where the different steps are applied on the adjacent nanopores on different branches after the reverse of the passage of the nucleic acid to redirect the nucleic acid through one of the adjacent nanopores.

16. The method of claim 11, wherein the adjustment of the electrical potentials allows the nucleic acid to be sorted into different fluid chambers connected to different branches of the branched nanochannel.

17. The method of claim 1, wherein the nanopores have a diameter from 2 nm to 100 nm.

18. The method of claim 1, wherein the adjacent nanopores are from 0.1 μm to 10 μm apart.

19. The method of claim 1, wherein the branched nanochannel has a diameter from 50 nm to 1000 nm.

20. The method of claim 1, wherein the branched nanochannel has a length from 5 μm to 100 μm.

* * * * *